United States Patent
Seino et al.

(10) Patent No.: US 12,358,894 B2
(45) Date of Patent: Jul. 15, 2025

(54) FLUORINE-CONTAINING PYRIMIDINE COMPOUND AND METHOD FOR PRODUCING SAME

(71) Applicant: UNIMATEC CO., LTD., Tokyo (JP)

(72) Inventors: Junya Seino, Kitaibaraki (JP); Rie Aotsu, Kitaibaraki (JP); Keisuke Kokin, Kitaibaraki (JP)

(73) Assignee: UNIMATEC CO., LTD. (JP)

( * ) Notice: Subject to any disclaimer, the term of this patent is extended or adjusted under 35 U.S.C. 154(b) by 705 days.

(21) Appl. No.: 17/773,231

(22) PCT Filed: Nov. 9, 2020

(86) PCT No.: PCT/JP2020/041738
§ 371 (c)(1),
(2) Date: Apr. 29, 2022

(87) PCT Pub. No.: WO2021/106539
PCT Pub. Date: Jun. 3, 2021

(65) Prior Publication Data
US 2022/0402893 A1 Dec. 22, 2022

(30) Foreign Application Priority Data
Nov. 25, 2019 (JP) .................................. 2019-212039

(51) Int. Cl.
*C07D 403/04* (2006.01)
(52) U.S. Cl.
CPC .................................. *C07D 403/04* (2013.01)
(58) Field of Classification Search
CPC .................................................. C07D 403/04
See application file for complete search history.

(56) References Cited

U.S. PATENT DOCUMENTS

| | | |
|---|---|---|
| 2004/0072692 A1 | 4/2004 | Hoffmann et al. |
| 2006/0122063 A1 | 6/2006 | Hoffmann et al. |
| 2008/0132522 A1 | 6/2008 | Rheinheimer et al. |
| 2015/0018353 A1 | 1/2015 | Kim et al. |
| 2015/0126364 A1 | 5/2015 | Pahutski, Jr. et al. |
| 2015/0342954 A1 | 12/2015 | Kim et al. |
| 2021/0283138 A1 | 9/2021 | Lee et al. |
| 2021/0403455 A1 | 12/2021 | Seino et al. |

FOREIGN PATENT DOCUMENTS

| | | |
|---|---|---|
| CN | 108059618 A | 5/2018 |
| JP | S59-104364 A | 6/1984 |
| WO | 1994-029300 A1 | 12/1994 |
| WO | 2004-013131 A2 | 2/2004 |
| WO | 2006-005571 A1 | 1/2006 |
| WO | 2007-048734 A1 | 5/2007 |

(Continued)

OTHER PUBLICATIONS

First Office Action for corresponding Chinese Patent Application No. 202080073671.4 dated Aug. 8, 2022, with English translation (16 Pages).
Notice of Reasons for Refusal for corresponding Japanese Application No. 2021-561269 dated Jun. 6, 2022, with English translation (4 Pages).
Decision of Rejection issued in corresponding Chinese Patent Application No. 202080073671.4 dated Apr. 13, 2023, with English translation (11 Pages).
Second Office Action for corresponding Chinese Patent Application No. 202080073671.4 dated Jan. 5, 2023, with English translation (14 Pages).
Office Action for corresponding Indian Patent Application No. 202237027398 dated Feb. 7, 2023, with English translation (6 Pages).
Extended European Search Report issued in corresponding Application No. 20891654.4 dated Sep. 27, 2023 (8 Pages).

(Continued)

*Primary Examiner* — Valerie Rodriguez-Garcia
(74) *Attorney, Agent, or Firm* — Harness, Dickey & Pierce, P.L.C.

(57) ABSTRACT

A fluorine-containing pyrimidine compound is provided represented by formula (1):

[Formula 1]

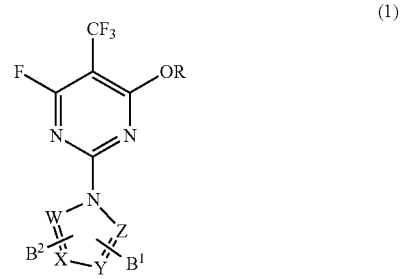

(1)

wherein in the above formula (1), R represents a hydrocarbon group having 1 to 12 carbon atoms, $B^1$ and $B^2$ each independently represent a hydrogen atom, a halogen atom, a hydrocarbon group having 1 to 10 carbon atoms, $-C_nF_{2n+1}$ where n is an integer of 1 to 10, a nitro group, a boronic acid group, $-OA^1$, $-SO_mA^1$ where m is an integer of 0 to 3, $-NA^1A^2$, $-COOA^1$ or $-CONA^1A^2$, W, X, Y and Z each independently represent CV or N, V represents a hydrogen atom, a halogen atom, a hydrocarbon group having 1 to 10 carbon atoms, $-C_nF_{2n+1}$ where n is an integer of 1 to 10, a nitro group, a boronic acid group, $-OA^1$, $-SO_mA^1$ where m is an integer of 0 to 3, $-NA^1A^2$, $-COOA^1$ or $-CONA^1A^2$, and $A^1$ and $A^2$ each independently represent a hydrogen atom or a hydrocarbon group having 1 to 10 carbon atoms.

6 Claims, No Drawings

(56) References Cited

FOREIGN PATENT DOCUMENTS

| WO | 2013-101830 A1 | 7/2013 |
|---|---|---|
| WO | 2013-173218 A1 | 11/2013 |
| WO | 2014-126954 A1 | 8/2014 |
| WO | 2017-152076 A1 | 9/2017 |
| WO | 2020-116296 A1 | 6/2020 |

OTHER PUBLICATIONS

International Search Report for corresponding International Application No. PCT/JP2020/041738, mailed Dec. 15, 2020, with English translation (7 Pages).

Inouye, Y. et al., Journal of Flourine Chemistry, 1985, vol. 27, No. 2, pp. 231-236, dated Nov. 6, 1984 (6 pages).

Munier-Lehmann, H. et al., "Original 2-(3-Alkoxy-1H-pyrazol-1-yl)pyrimidine Derivatives as Inhibitors of Human Dihydroorotate Dehydrogenase (DHODH)" Journal of Medicinal Chemistry, 2015, vol. 58, 860-877, dated Jan. 6, 2015 (3 pages).

Zhang, P. et al., "Direct regioselective Csp2-H trifluoromethylation of pyrimidinones and pyridinones" Tetrahedron, 2016, vol. 72, 3250-3255, dated Jun. 9, 2016 (3 pages).

Yang, B. et al., "Visible-Light Photoredox Decarboxylation of Perfluoroarene Iodine(III) Trifluoroacetates for C—H Trifluoromethylation of (Hetero)arenes" ACS Catalysis, 2018, vol. 8, pp. 2839-2843, dated Mar. 1, 2018 (2 pages).

Ouyang, Yao et al., "Trifluoromethanesulfonic Anhydride as a Low-Cost and Versatile Trifluoromethylation Reagent" Angewandte Chemie International Edition, 2018 vol. 57, pp. 6926-6929, dated Apr. 19, 2018 (2 pages).

Written Opinion of the International Searching Authority for corresponding International Application No. PCT/JP2020/041738 mailed Dec. 15, 2020, with English translation (6 Pages).

International Preliminary Report on Patentability for corresponding International Application No. PCT/JP2020/041738 mailed Dec. 15, 2020, with English translation (7 Pages).

FLUORINE-CONTAINING PYRIMIDINE COMPOUND AND METHOD FOR PRODUCING SAME

CROSS REFERENCE TO RELATED APPLICATIONS

This is the National Stage of International Application No. PCT/JP2020/041738, filed Nov. 9, 2020, which claims the benefit of Japanese Patent Application No. 2019-212039 filed Nov. 25, 2019. The contents of these applications are incorporated hereby by reference in their entirety.

BACKGROUND

Technical Field

The present disclosure relates to a fluorine-containing pyrimidine compound and a method for producing the same.

Related Art

Conventionally, fluorine-containing pyrimidine compounds have been reported to have various biological activities. Among them, a compound having a pyrazole ring or a triazole ring or the like as a substituent at the 2-position of the pyrimidine ring is expected to be used in the fields of medicine and agrochemicals.

More specifically, Journal Of Medicinal Chemistry, Vol. 58, 2015, pp. 860-877 discloses a compound having a pyrazole ring at the 2-position of a pyrimidine ring. Journal Of Medicinal Chemistry, Vol. 58, 2015, pp. 860-877 reports that a compound having a 2-(1-pyrazolyl)-pyrimidine structure has an inhibitory effect on growth of measles virus and chikungunya virus.

Moreover, International Publication No. WO 2017/152076 discloses a compound having a triazole ring at the 2-position of a pyrimidine ring. International Publication No. WO 2017/152076 reports that a compound having a 2-(1-triazolyl)-pyrimidine structure has an anti-tumor activity.

From such viewpoints, introduction of substituents to the 4-, 5-, and 6-positions of the pyrimidine ring has drawn attention in anticipation of further improvement in the activity.

Tetrahedron, Vol. 72, 2016, pp. 3250-3255, ACS Catalysis, Vol. 8, 2018, pp. 2839-2843, and Angewandte Chemie International Edition, Vol. 57, 2018, pp. 6926-6929 disclose, on the other hand, a method for synthesizing a pyrimidine compound having a trifluoromethyl group at the 5-position of a pyrimidine ring and substituents at the 4-position and the 6-position. More specifically, Tetrahedron, Vol. 72, 2016, pp. 3250-3255 reports a synthetic method using sodium trifluoromethanesulfinate (Langlois reagent), ACS Catalysis, Vol. 8, 2018, pp. 2839-2843 reports a synthetic method using a trifluoroacetic acid derivative, and Angewandte Chemie International Edition, Vol. 57, 2018, pp. 6926-6929 reports a synthetic method using trifluoromethanesulfonic acid anhydride.

TECHNICAL PROBLEM

However, from the viewpoint of reactivity and selectivity, conventionally, it has been difficult to produce a fluorine-containing pyrimidine compound having a fluorine-containing substituent at the 5-position of the pyrimidine ring, a heterocyclic ring as a substituent at the 2-position, and substituents at the 4-position and the 6-position, and such a fluorine-containing pyrimidine compound has not been reported. The fluorine-containing pyrimidine compound is expected to have various biological activities, and a novel fluorine-containing pyrimidine compound having substituents at the 4- and 6-positions of a pyrimidine ring and a heterocyclic ring as a substituent at the 2-position, and establishment of a production method therefor, have been desired.

In the production method reported in Tetrahedron, Vol. 72, 2016, pp. 3250-3255, the regioselectivity upon introduction of a trifluoromethyl group is low, which thereby raises a concern of decreasing introduction efficiency of trifluoromethyl group for a substrate having a plurality of heterocyclic rings such as a pyrimidine compound substituted with a heterocyclic ring, or a concern of difficulty in introducing a trifluoromethyl group. Moreover, there have been problems such as not only using 3 times an amount of Langlois reagent as a trifluoromethylating agent with respect to the substrate but also using manganese acetate (III) hydrate that is harmful as an oxidizing agent in an amount 3 times that of the substrate.

It is considered that by further modification and derivatization of the compound obtained by the production methods reported in ACS Catalysis, Vol. 8, 2018, pp. 2839-2843 and Angewandte Chemie International Edition, Vol. 57, 2018, pp. 6926-6929, it is converted into the fluorine-containing pyrimidine compound. However, there have been cases where complexity and reduction in efficiency due to an increase in the number of steps are unavoidable, or the production of the fluorine-containing pyrimidine compound itself is difficult. Further, the production methods are considered to be unsuitable for practical use because irradiation with light in the presence of a ruthenium complex catalyst is necessary, and also because use of the trifluoromethylating agent in an amount of 2.5 to 3 times the amount of substrate is required in ACS Catalysis, Vol. 8, 2018, pp. 2839-2843, and use of the trifluoromethylating agent in an amount of 3 times the amount of substrate is required in Angewandte Chemie International Edition, Vol. 57, 2018, pp. 6926-6929.

SUMMARY

Then, the present inventors have found that an azole structure in which all heteroatoms are nitrogen, such as a pyrazole ring structure or a triazole ring structure can be introduced at the 2-position between the two nitrogen atoms on a pyrimidine ring by reacting a specific raw material, and thus have completed the present disclosure. Namely, the present disclosure provides a novel fluorine-containing pyrimidine compound that has substituents at the 4-position and 6-position of the pyrimidine ring and an azole structure in which all heteroatoms are nitrogen as a substituent at the 2-position, which has not been known conventionally, and a production method capable of easily producing the fluorine-containing pyrimidine compound.

The configuration of the present disclosure is as follows.

[1] An aspect of the present disclosure is a fluorine-containing pyrimidine compound represented by the following formula (1):

[Formula 1]

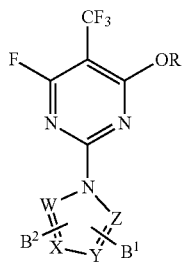

(1)

wherein
R represents a hydrocarbon group having 1 to 12 carbon atoms,
$B^1$ and $B^2$ each independently represent a hydrogen atom, a halogen atom, a hydrocarbon group having 1 to 10 carbon atoms, —$C_nF_{2n+1}$ where n is an integer of 1 to 10, a nitro group, a boronic acid group, —$OA^1$, —$SO_mA^1$ where m is an integer of 0 to 3, —$NA^1A^2$, —$COOA^1$ or –$CONA^1A^2$,
W, X, Y and Z each independently represent CV or N,
V represents a hydrogen atom, a halogen atom, a hydrocarbon group having 1 to 10 carbon atoms, —$C_nF_{2n+1}$ where n is an integer of 1 to 10, a nitro group, a boronic acid group, —$OA^1$, —$SO_mA^1$ where m is an integer of 0 to 3, —$NA^1A^2$, —$COOA^1$ or —$CONA^1A^2$, and
$A^1$ and $A^2$ each independently represent a hydrogen atom or a hydrocarbon group having 1 to 10 carbon atoms.

[2] In the aspect of the present disclosure, R is an alkyl group having 1 to 10 carbon atoms.

[3] Another aspect of the present disclosure is a method for producing a fluorine-containing pyrimidine compound, including: a step of reacting a fluoroisobutylene derivative represented by the following formula (2) with a compound represented by the following formula (3) or a salt thereof to obtain a fluorine-containing pyrimidine compound of the following formula (1):

[Formula 2]

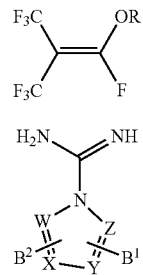

(2)

(3)

(1)

wherein
R represents a hydrocarbon group having 1 to 12 carbon atoms,
$B^1$ and $B^2$ each independently represent a hydrogen atom, a halogen atom, a hydrocarbon group having 1 to 10 carbon atoms, —$C_nF_{2n+1}$ where n is an integer of 1 to 10, a nitro group, a boronic acid group, —$OA^1$, —$SO_mA^1$ where m is an integer of 0 to 3, —$NA^1A^2$, —$COOA^1$ or —$CONA^1A^2$,
W, X, Y and Z each independently represent CV or N,
V represents a hydrogen atom, a halogen atom, a hydrocarbon group having 1 to 10 carbon atoms, —$C_nF_{2n+1}$ where n is an integer of 1 to 10, a nitro group, a boronic acid group, —$OA^1$, —$SO_mA^1$ where m is an integer of 0 to 3, —$NA^1A^2$, —$COOA^1$ or —$CONA^1A^2$, and
$A^1$ and $A^2$ each independently represent a hydrogen atom or a hydrocarbon group having 1 to 10 carbon atoms.

[4] Another aspect of the present disclosure is a method for producing a fluorine-containing pyrimidine compound, including: a step of reacting a fluoroisobutane derivative represented by the following formula (4) with a compound represented by the following formula (3) or a salt thereof to obtain a fluorine-containing pyrimidine compound of the following formula (1):

[Formula 3]

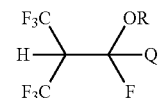

(4)

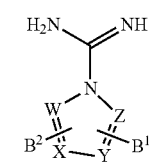

(3)

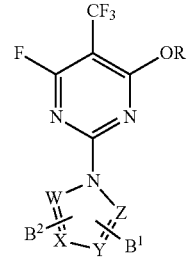

(1)

wherein
Q represents a halogen atom, —$OA^1$, —$SO_mA^1$ where m is an integer of 0 to 3, or —$NA^1A^2$,
R represents a hydrocarbon group having 1 to 12 carbon atoms,
$B^1$ and $B^2$ each independently represent a hydrogen atom, a halogen atom, a hydrocarbon group having 1 to 10 carbon atoms, —$C_nF_{2n+1}$ where n is an integer of 1 to 10, a nitro group, a boronic acid group, —$OA^1$, —$SO_mA^1$ where m is an integer of 0 to 3, —$NA^1A^2$, —$COOA^1$ or —$CONA^1A^2$,
W, X, Y and Z each independently represent CV or N,
V represents a hydrogen atom, a halogen atom, a hydrocarbon group having 1 to 10 carbon atoms, —$C_nF_{2n+1}$ where n is an integer of 1 to 10, a nitro group, a boronic acid group, —$OA^1$, —$SO_mA^1$ where m is an integer of 0 to 3, —$NA^1A^2$, —$COOA^1$ or —$CONA^1A^2$, and $A^1$ and $A^2$ each independently represent a hydrogen atom or a hydrocarbon group having 1 to 10 carbon atoms.

[5] In the aspect of the present disclosure according to the method for producing a fluorine-containing pyrimidine compound, wherein R is an alkyl group having 1 to 10 carbon atoms.

EFFECTS OF INVENTION

A novel fluorine-containing pyrimidine compound having substituents at the 4-position and 6-position of the pyrimidine ring, and an azole structure in which all heteroatoms are nitrogen at the 2-position, and a production method capable of easily producing the fluorine-containing pyrimidine compound, can be provided.

DETAILED DESCRIPTION

Hereinafter, embodiments of the present disclosure will be described in detail. However, the scope of the present disclosure is not limited to the specific examples described below.

Fluorine-Containing Pyrimidine Compound

The fluorine-containing pyrimidine compound in one embodiment is represented by the following formula (1):

[Formula 4]

(1)

wherein in the above formula (1),
R represents a hydrocarbon group having 1 to 12 carbon atoms,
$B^1$ and $B^2$ each independently represent a hydrogen atom, a halogen atom, a hydrocarbon group having 1 to 10 carbon atoms, $-C_nF_{2n+1}$ (n is an integer of 1 to 10), a nitro group, a boronic acid group, $-OA^1$, $-SO_mA^1$ (m is an integer of 0 to 3), $-NA^1A^2$, $-COOA^1$ or $-CONA^1A^2$,
W, X, Y and Z each independently represent CV or N,
V represents a hydrogen atom, a halogen atom, a hydrocarbon group having 1 to 10 carbon atoms, $-C_nF_{2n+1}$ (n is an integer of 1 to 10), a nitro group, a boronic acid group, $-OA^1$, $-SO_mA^1$ (m is an integer of 0 to 3), $-NA^1A^2$, $-COOA^1$ or $-CONA^1A^2$, and
$A^1$ and $A^2$ each independently represent a hydrogen atom or a hydrocarbon group having 1 to 10 carbon atoms.

R is not particularly limited as long as it is a hydrocarbon group having 1 to 12 carbon atoms and is composed of a carbon atom and a hydrogen atom, and includes a chain hydrocarbon group, an aromatic hydrocarbon group, an alicyclic hydrocarbon group and the like. The chain hydrocarbon group is not particularly limited as long as the total number of carbon atoms is 1 to 12, and may be a linear hydrocarbon group or a branched chain hydrocarbon group.

When R is an aromatic hydrocarbon group, the aromatic hydrocarbon group is not particularly limited as long as the total number of carbon atoms is 6 to 12, and may be an aromatic hydrocarbon group having a substituent or an aromatic hydrocarbon group having no substituent. Moreover, the aromatic hydrocarbon group may have a condensed polycyclic structure. When R is an alicyclic hydrocarbon group, the alicyclic hydrocarbon group is not particularly limited as long as the total number of carbon atoms is 3 to 12, and may be an alicyclic hydrocarbon group having a substituent or an alicyclic hydrocarbon group having no substituent. Further, the alicyclic hydrocarbon group may have a bridged ring structure.

Examples of the chain hydrocarbon group include alkyl groups such as a methyl group, an ethyl group, a n-propyl group, an i-propyl group, a n-butyl group, an i-butyl group, a sec-butyl group, a ter-butyl group, a pentyl group, a hexyl group, a heptyl group, an octyl group, a nonyl group, a decyl group, an undecyl group and a dodecyl group;

alkenyl groups such as an ethenyl group, a propenyl group, a butenyl group, a pentenyl group, a hexenyl group, a heptenyl group, an octenyl group, a nonenyl group, a decenyl group, an undecenyl group and a dodecenyl group; and alkynyl groups such as an ethynyl group, a propynyl group, a butynyl group, a pentynyl group, a hexynyl group, a heptynyl group, an octynyl group, a nonynyl group, a decynyl group, an undecynyl group and a dodecynyl group.

Examples of the aromatic hydrocarbon group include a phenyl group and a naphthyl group.

Examples of the alicyclic hydrocarbon group include a saturated or unsaturated cyclic hydrocarbon group, and examples of the cyclic hydrocarbon group include a cyclopropyl group, a cyclobutyl group, a cyclohexyl group, a cyclopentyl group, an adamantyl group and a norbornyl group.

R is preferably an alkyl group having 1 to 10 carbon atoms. R being an alkyl group having 1 to 10 carbon atoms enables the fluoroisobutylene derivative of formula (2) and the fluoroisobutane derivative of formula (4), which are raw materials of the fluorine-containing pyrimidine compound, to be easily prepared.

$B^1$ and $B^2$ each independently represent a hydrogen atom, a halogen atom, a hydrocarbon group having 1 to 10 carbon atoms, $-C_nF_{2n+1}$ (n is an integer of 1 to 10), a nitro group, a boronic acid group, $-OA^1$, $-SO_mA^1$ (m is an integer of 0 to 3), $-NA^1A^2$, $-COOA^1$ or $-CONA^1A^2$, and each preferably represent a hydrogen atom, a halogen atom or a hydrocarbon group having 1 to 10 carbon atoms. $B^1$ and $B^2$ may be the same or different from each other.

In $B^1$ and $B^2$, the halogen atom is F, Cl, Br or I, and preferably F or Cl.

In $B^1$ and $B^2$, the hydrocarbon group having 1 to 10 carbon atoms is not particularly limited as long as it is a hydrocarbon group composed of a carbon atom and a hydrogen atom, and can be, for example, a hydrocarbon group having 1 to 10 carbon atoms in R described above.

In $B^1$ and $B^2$, $-C_nF_{2n+1}$ is not particularly limited as long as it is a perfluoroalkyl group composed of a carbon atom and a fluorine atom, and may be linear or branched. In addition, n is an integer of 1 to 10, and preferably an integer of 1 to 3.

In $B^1$ and $B^2$, $A^1$ included in $-OA^1$ and $-SO_mA^1$ represents a hydrogen atom or a hydrocarbon group having 1 to 10 carbon atoms. When $A^1$ represents a hydrocarbon group having 1 to 10 carbon atoms, it can be, for example, a hydrocarbon group having 1 to 10 carbon atoms in R described above. Further, m is an integer of 0 to 3, preferably an integer of 0 to 2, and more preferably an integer of 0 to 1.

In $B^1$ and $B^2$, $A^1$ and $A^2$ included in —$NA^1A^2$ each independently represent a hydrogen atom or a hydrocarbon group having 1 to 10 carbon atoms. $A^1$ and $A^2$ may be the same or different from each other. When $A^1$ and $A^2$ represent a hydrocarbon group having 1 to 10 carbon atoms, they can be, for example, hydrocarbon groups having 1 to 10 carbon atoms in R described above.

In $B^1$ and $B^2$, $A^1$ included in —$COOA^1$ represents a hydrogen atom or a hydrocarbon group having 1 to 10 carbon atoms. When $A^1$ represents a hydrocarbon group having 1 to 10 carbon atoms, it can be, for example, a hydrocarbon group having 1 to 10 carbon atoms in R described above.

In $B^1$ and $B^2$, $A^1$ and $A^2$ included in —$CONA^1A^2$ each independently represent a hydrogen atom or a hydrocarbon group having 1 to 10 carbon atoms. $A^1$ and $A^2$ may be the same or different from each other. When $A^1$ and $A^2$ represent a hydrocarbon group having 1 to 10 carbon atoms, they can be, for example, hydrocarbon groups having 1 to 10 carbon atoms in R described above.

W, X, Y and Z each independently represent CV or N. When at least one selected from W, X, Y and Z is CV, V represents a hydrogen atom, a halogen atom, a hydrocarbon group having 1 to 10 carbon atoms, —$C_nF_{2n+1}$ (n is an integer of 1 to 10), a nitro group, a boronic acid group, —$OA^1$, —$SO_mA^1$ (m is an integer of 0 to 3), —$NA^1A^2$,— $COOA^1$ or —$CONA^1A^2$, and preferably represents a hydrogen atom, a halogen atom or a hydrocarbon group having 1 to 10 carbon atoms. It is preferable that at least one selected from W, X, Y and Z be N, and it is more preferable that any one or two selected from W, X, Y and Z be N. In particular, the fluorine-containing pyrimidine compound represented by formula (1) preferably has a pyrazole ring structure or a triazole ring structure at the 2-position on the pyrimidine ring.

In V, the halogen atom is F, Cl, Br or I, and preferably F or Cl.

In V, the hydrocarbon group having 1 to 10 carbon atoms is not particularly limited as long as it is a hydrocarbon group composed of a carbon atom and a hydrogen atom, and can be, for example, a hydrocarbon group having 1 to 10 carbon atoms in R described above.

In V, —$C_nF_{2n+1}$ is not particularly limited as long as it is a perfluoroalkyl group composed of a carbon atom and a fluorine atom, and may be linear or branched. In addition, n is an integer of 1 to 10, and preferably an integer of 1 to 3.

In V, $A^1$ included in —$OA^1$ and —$SO_mA^1$ represents a hydrogen atom or a hydrocarbon group having 1 to 10 carbon atoms. When $A^1$ represents a hydrocarbon group having 1 to 10 carbon atoms, it can be, for example, a hydrocarbon group having 1 to 10 carbon atoms in R described above. Further, m is an integer of 0 to 3, preferably an integer of 0 to 2, and more preferably an integer of 0 to 1.

In V, $A^1$ and $A^2$ included in —$NA^1A^2$ each independently represent a hydrogen atom or a hydrocarbon group having 1 to 10 carbon atoms. $A^1$ and $A^2$ may be the same or different from each other. When $A^1$ and $A^2$ represent a hydrocarbon group having 1 to 10 carbon atoms, they can be, for example, hydrocarbon groups having 1 to 10 carbon atoms in R described above.

In V, $A^1$ included in —$COOA^1$ represents a hydrogen atom or a hydrocarbon group having 1 to 10 carbon atoms. When $A^1$ represents a hydrocarbon group having 1 to 10 carbon atoms, it can be, for example, a hydrocarbon group having 1 to 10 carbon atoms in R described above.

In V, $A^1$ and $A^2$ included in —$CONA^1A^2$ each independently represent a hydrogen atom or a hydrocarbon group having 1 to 10 carbon atoms. $A^1$ and $A^2$ may be the same or different from each other. When $A^1$ and $A^2$ represent a hydrocarbon group having 1 to 10 carbon atoms, they can be, for example, hydrocarbon groups having 1 to 10 carbon atoms in R described above.

The fluorine-containing pyrimidine compound in one embodiment has a specific substituent (an azole structure in which all heteroatoms are nitrogen, such as a pyrazole ring structure and a triazole ring structure) at the 2-position of the pyrimidine ring, and specific substituents (—OR, —$CF_3$ and —F) at the 4-position, 5-position and 6-position of the pyrimidine ring, and thereby it can have an excellent effect from the viewpoint of structural expandability. In particular, desired biological activity (for example, growth inhibitory activity on various viruses, antibacterial activity against various bacteria, antitumor activity) can be expected, and for example, control activity on pathogens of rice blast and the like can be expected. The azole structure in which all heteroatoms are nitrogen located on the 2-position of the pyrimidine ring may or may not further have a substituent. The azole structure having a substituent can further impart properties to the fluorine-containing pyrimidine compound in one embodiment. Moreover, the substituents on the 4- and 6-positions of the pyrimidine ring being different groups (—OR and —F) facilitates derivatization into an asymmetric structure, which can also be expected to be used as an intermediate. More specifically, reacting the fluorine-containing pyrimidine compound under acidic conditions to modify —OR can provide a derivative. Moreover, reacting the fluorine-containing pyrimidine compound under basic conditions to modify -F can provide a derivative. The fluorine-containing pyrimidine compound in one embodiment is useful in the field of, for example, electronic materials such as organic semiconductors and liquid crystals.

Method for Producing Fluorine-Containing Pyrimidine Compound

A method for producing a fluorine-containing pyrimidine compound in one embodiment includes (a) a step of reacting a fluoroisobutylene derivative represented by the following formula (2) with a compound represented by the following formula (3) or a salt thereof to obtain a fluorine-containing pyrimidine compound of the following formula (1):

[Formula 5]

(2)

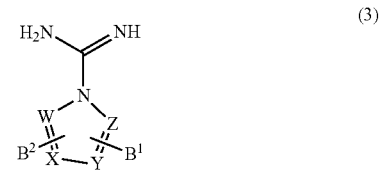

(3)

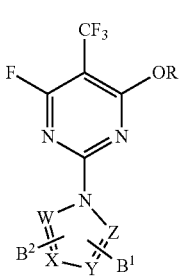

(1)

wherein in the above formulae (1) to (3),

R represents a hydrocarbon group having 1 to 12 carbon atoms, $B^1$ and $B^2$ each independently represent a hydrogen atom, a halogen atom, a hydrocarbon group having 1 to 10 carbon atoms, —$C_nF_{2n+1}$ (n is an integer of 1 to 10), a nitro group, a boronic acid group, —$OA^1$, —$SO_mA^1$ (m is an integer of 0 to 3), —$NA^1A^2$, —$COOA^1$ or —$CONA^1A^2$, W, X, Y and Z each independently represent CV or N, V represents a hydrogen atom, a halogen atom, a hydrocarbon group having 1 to 10 carbon atoms, —$C_nF_{2n+1}$ (n is an integer of 1 to 10), a nitro group, a boronic acid group, —$OA^1$, —$SO_mA^1$ (m is an integer of 0 to 3), —$NA^1A^2$, —$COOA^1$ or —$CONA^1A^2$, and $A^1$ and $A^2$ each independently represent a hydrogen atom or a hydrocarbon group having 1 to 10 carbon atoms.

In formula (2), R is the same as that defined in the compounds of formula (1) described above, and in formula (3), each of $B^1$, $B^2$, W, X, Y and Z is the same as that defined in the compounds of formula (1) described above.

R in the above formula (2) preferably represents an alkyl group having 1 to 10 carbon atoms. R in formula (2) can be, for example, an alkyl group having 1 to 10 carbon atoms in R in formula (1) described above.

A reaction of (a) above between the fluoroisobutylene derivative represented by formula (2) and the compound represented by formula (3) is represented by the following reaction formula (A).

[Formula 6]

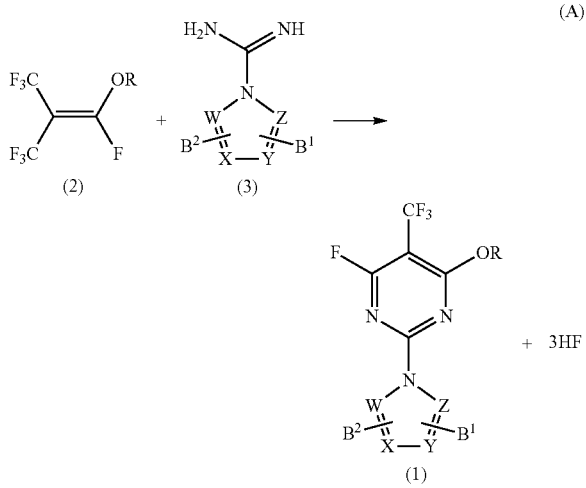

In the above reaction formula (A), the compounds of the above formula (3) each may be in the form of salt. Examples of the compounds of formula (3) in the form of salts include a compound in a form of at least one of the amino moiety (—$NH_2$) and the imino moiety (=NH) constituting the amidino group of the compounds of formula (3), being cationized to (—$NH_3^+$) and (=$NH_2^+$) to form a salt with the counterion. The counterion is not particularly limited as long as it is a monovalent anion, and includes, for example, halide ions such as $F^-$, $Cl^-$, $Br^-$ and $I^-$.

In the method for producing a fluorine-containing pyrimidine compound in one embodiment, for example, the reactions of (a) above can be carried out in one step in the presence of a hydrogen halide scavenger. Therefore, the fluorine-containing pyrimidine compounds of the above formula (1) can be easily obtained. In the reactions of (a) above, a cyclic pyrimidine structure is formed between the fluoroisobutylene derivative represented by formula (2) and the amidino group of the compounds of formula (3). At the 2-position of the pyrimidine structure, a group derived from the azole structure in which all heteroatoms are nitrogen in the compound of formula (3) is located. Further, —OR, $CF_3$ and F derived from the fluoroisobutylene derivative are located at the 4-position, 5-position and 6-position of the pyrimidine structure, respectively.

The hydrogen halide scavenger is a substance having a function of capturing hydrogen fluoride (HF) formed from a hydrogen atom derived from the amidino group in the compounds of formula (3) and a fluorine atom derived from the fluoroisobutylene derivative of formula (2), in the reaction formula (A). As the hydrogen halide scavenger, an inorganic compound such as sodium hydroxide, potassium hydroxide, calcium hydroxide, sodium carbonate, potassium carbonate, sodium fluoride and potassium fluoride, and an organic nitrogen derivative such as pyridine, triethylamine, diisopropylethylamine, diazabicyclononene, diazabicycloundecene, methyltriazabicyclodecene and diazabicyclooctane, can be used.

The step of (A) above obtaining a fluorine-containing pyrimidine compound is preferably carried out in the presence of a fluoride ion scavenger. The fluoroisobutylene derivative represented by the above formula (2) and the compound represented by the above formula (3) or a salt thereof are preferably reacted in the presence of, as a fluoride ion scavenger, a salt of a cation of lithium, sodium, magnesium, potassium, calcium or tetramethylammonium, and an anion of trifluoroacetic acid, heptafluorobutyric acid, methanesulfonic acid, ethanesulfonic acid, benzenesulfonic acid, toluenesulfonic acid, trifluoromethanesulfonic acid, nonafluorobutanesulfonic acid, bis(trifluoromethanesulfonyl)imide, bis(nonafluorobutanesulfonyl)imide, N,N-hexafluoropropane-1,3-disulfonyl imide, tetraphenylboric acid, tetrakis[3,5-bis(trifluoromethyl)phenyl] boric acid or tetrakis(pentafluorophenyl) boric acid. Among these, the potassium or sodium salt is preferably used, and the sodium salt is more preferably used. It is conjectured that the cation derived from the fluoride ion scavenger captures a fluoride ion isolated from the fluoroisobutylene derivative represented by formula (2) during the reaction, resulting in precipitation as a salt having low solubility in organic solvents, and thereby accelerating the reaction and producing the fluorine-containing pyrimidine compound represented by the above formula (1) in high yield.

A reaction temperature upon reactions (a) above is preferably 0 to 100° C., more preferably 5 to 50° C., and still more preferably 10 to 20° C. A reaction time upon reactions (a) above is preferably 0.5 to 48 hours, more preferably 1 to 36 hours, and still more preferably 2 to 12 hours.

A solvent used in the reactions of (a) above includes aprotic polar solvents such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide and sulfolane, or two-phase solvents of a protonic polar solvent such as water and a water-insoluble solvent such as dichloromethane, toluene and diethyl ether. Moreover, as a catalyst for the reactions of (a) above, quaternary ammonium halides such as benzyltriethylammonium chloride, a quaternary phosphonium halide and crown ether can be used.

A method for producing a fluorine-containing pyrimidine compound in another embodiment includes (b) a step of reacting a fluoroisobutane derivative represented by the following formula (4) with a compound represented by the following formula (3) or a salt thereof to obtain a fluorine-containing pyrimidine compound of the following formula (1):

[Formula 7]

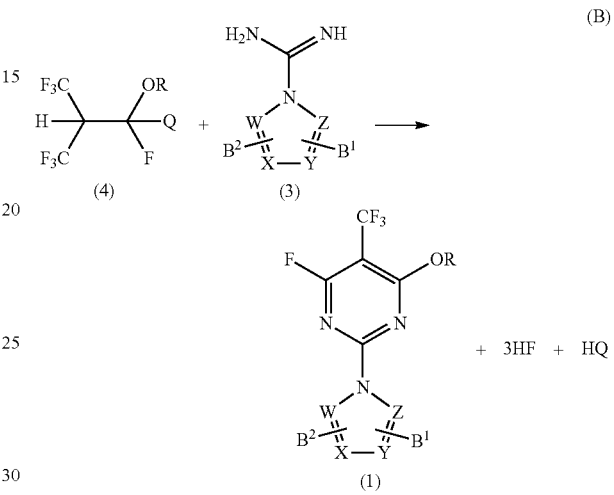

wherein in the above formula (1), (3) or (4),
Q represents a halogen atom, —OA$^1$, —SO$_m$A$^1$ (m is an integer of 0 to 3) or —NA$^1$A$^2$,
R represents a hydrocarbon group having 1 to 12 carbon atoms,
B$^1$ and B$^2$ each independently represent a hydrogen atom, a halogen atom, a hydrocarbon group having 1 to 10 carbon atoms, —C$_n$F$_{2n+1}$ (n is an integer of 1 to 10), a nitro group, a boronic acid group, —OA$^1$, —SO$_m$A$^1$ (m is an integer of 0 to 3), —NA$^1$A$^2$, —COOA$^1$ or —CONA$^1$A$^2$,
W, X, Y and Z each independently represent CV or N,
V represents a hydrogen atom, a halogen atom, a hydrocarbon group having 1 to 10 carbon atoms, —C$_n$F$_{2n+1}$ (n is an integer of 1 to 10), a nitro group, a boronic acid group, —OA$^1$, —SO$_m$A$^1$ (m is an integer of 0 to 3), —NA$^1$A$^2$, —COOA$^1$ or —CONA$^1$A$^2$, and
A$^1$ and A$^2$ each independently represent a hydrogen atom or a hydrocarbon group having 1 to 10 carbon atoms.

In formula (4), R is the same as that defined in the compound of formula (1) described above, and the halogen atom, —OA$^1$, —SO$_m$A$^1$ (m is an integer of 0 to 3) and —NA$^1$A$^2$ are the same as those defined in the compound of formula (1) described above.

R in the above formulae (1) and (4) preferably represents an alkyl group having 1 to 10 carbon atoms. R in formula (4) can be, for example, an alkyl group having 1 to 10 carbon atoms in R in formula (1) described above.

A reaction of (b) above between the fluoroisobutane derivative represented by formula (4) and the compound represented by formula (3) is represented by the following reaction formula (B).

[Formula 8]

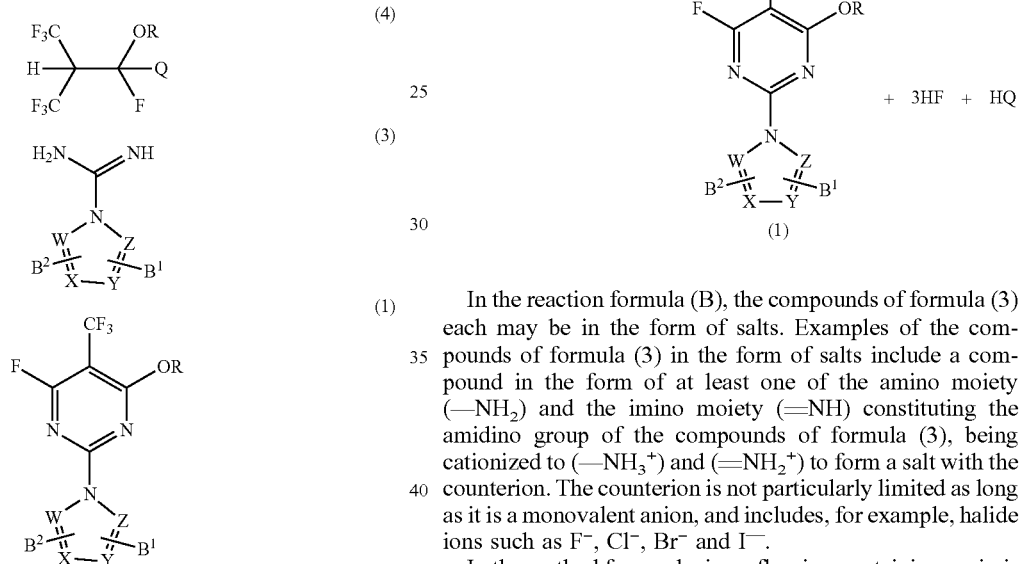

In the reaction formula (B), the compounds of formula (3) each may be in the form of salts. Examples of the compounds of formula (3) in the form of salts include a compound in the form of at least one of the amino moiety (—NH$_2$) and the imino moiety (=NH) constituting the amidino group of the compounds of formula (3), being cationized to (—NH$_3^+$) and (=NH$_2^+$) to form a salt with the counterion. The counterion is not particularly limited as long as it is a monovalent anion, and includes, for example, halide ions such as F$^-$, Cl$^-$, Br$^-$ and I$^-$.

In the method for producing a fluorine-containing pyrimidine compound in the other embodiment, for example, the reactions of (B) above can be carried out in one step. Therefore, the fluorine-containing pyrimidine compounds of the above formula (1) can be easily obtained. In the reactions of (b) above, a cyclic pyrimidine structure is formed between the fluoroisobutane derivative represented by formula (4) and the amidino group of the compounds of formula (3). At the 2-position of the pyrimidine structure, a group derived from the azole structure in which all heteroatoms are nitrogen in the compound of formula (3) is located. Further, —OR, CF$_3$ and F derived from the fluoroisobutane derivative are located at the 4-position, 5-position and 6-position of the pyrimidine structure, respectively.

A reaction temperature upon reactions (b) above is preferably 0 to 100° C., more preferably 5 to 50° C., and still more preferably 10 to 20° C. A reaction time upon reactions (b) above is preferably 0.5 to 48 hours, more preferably 1 to 36 hours, and still more preferably 4 to 24 hours. In the reactions of (b) above, the same hydrogen halide scavengers as those of (a) above may be used.

A solvent used in the reactions of (b) above includes aprotic polar solvents such as tetrahydrofuran, monoglyme, diglyme, triglyme, tetraglyme, acetonitrile, dimethylformamide, dimethylacetamide, methylpyrrolidone, dimethylethyleneurea, tetramethylurea, dimethylsulfoxide and sulfolane, or two-phase solvents of a protonic polar solvent such as water and a water-insoluble solvent such as dichloromethane, toluene and diethyl ether. Moreover, as a catalyst for the reactions of (b) above, quaternary ammonium halides such as benzyltriethylammonium chloride, a quaternary phosphonium halide and crown ether can be used.

Although the embodiments of the present disclosure have been described above, the present disclosure is not limited to the aforementioned embodiments, and includes all aspects included in the concept and claims of the present disclosure, and can be variously modified within the scope of the present disclosure.

EXAMPLES

Hereinafter, Examples of the present disclosure will be described, but the present disclosure is not limited to these Examples as long as the gist of the present disclosure is not exceeded. Moreover, room temperature denotes a temperature within the range of 20° C. ±5° C. unless otherwise specified.

Example 1

Production of 6-fluoro-4-methoxy-2-(1-pyrazolyl)-5-(trifluoromethyl)pyrimidine

Under ice-water cooling, to 33 g of tetrahydrofuran were added 2 g (13.6 mmol) of 1-amidinopyrazole hydrochloride, 17.4 g (54.4 mmol) of potassium bis(trifluoromethanesulfonyl)imide and 3.3 g (15.6 mmol) of 1,3,3,3-tetrafluoro-1-methoxy-2-(trifluoromethyl)-1-propene. Subsequently, a mixed solution of 9.2 g (71 mmol) of diisopropylethylamine and 10 g of tetrahydrofuran was added dropwise such that the internal temperature did not exceed 10° C., and the temperature was raised to room temperature. After about 64 hours, tetrahydrofuran was distilled off under reduced pressure, and then the residue was dissolved in ethyl acetate followed by column purification to obtain 2.4 g of the compound represented by the following formula (5) (chemical formula: $C_9H_6F_4N_4O$, molecular weight: 262.17 g/mol). The isolated yield of the obtained compound was 67%.

[Formula 9]

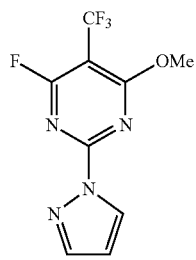

(5)

The analysis results were as follows.
Mass Spectrum (APCI, m/z): 262 ([M]$^+$)
$^1$H-NMR (300 MHz, CDCl$_3$) δ ppm: 8.52 (dd, 1H), 7.88 (d, 1H), 6.54 (m, 1H), 4.25 (s, 3H)
$^{19}$F-NMR (300 MHz, C$_6$F$_6$) δ ppm: −58.51 (dd, 1F), −58.57 (d, 3F)

Example 2

Production of 6-fluoro-4-methoxy-2-(1-triazolyl)-5-(trifluoromethyl)pyrimidine

Under ice-water cooling, to 20 g of tetrahydrofuran were added 1 g (6.8 mmol) of 1-amidinotriazole hydrochloride, 8.7 g (27 mmol) of potassium bis(trifluoromethanesulfonyl)imide and 1.7 g (7.8 mmol) of 1,3,3,3-tetrafluoro-1-methoxy-2-(trifluoromethyl)-1-propene. Subsequently, a mixed solution of 4.6 g (35 mmol) of diisopropylethylamine and 10 g of tetrahydrofuran was added dropwise such that the internal temperature did not exceed 10° C., and the temperature was raised to room temperature. After about 16 hours, tetrahydrofuran was distilled off under reduced pressure, and then the residue was dissolved in ethyl acetate followed by column purification to obtain 70 mg of the compound represented by the following formula (6) (chemical formula: $C_8H_5F_4N_5O$, molecular weight: 263.16 g/mol). The isolated yield of the obtained compound was 4%.

[Formula 10]

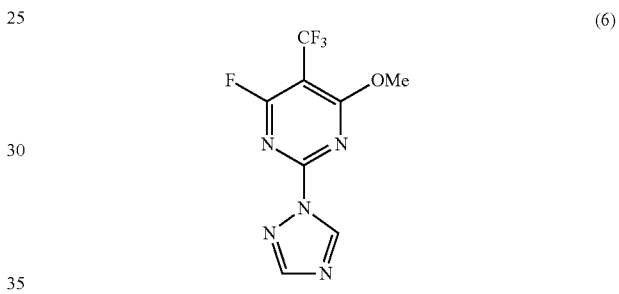

(6)

The analysis results were as follows.
Mass Spectrum (APCI, m/z): 263 ([M]$^+$)
$^1$H-NMR (300 MHz, CDCl$_3$) δ ppm: 9.19 (s, 1H), 8.20 (s, 1H), 4.29 (s, 3H)
$^{19}$F-NMR (300 MHz, C$_6$F$_6$) δ ppm: −57.40 (dd, 1F), −58.86 (d, 3F)

Example 3

Production of 6-fluoro-4-methoxy-2-(1-pyrazolyl)-5-(trifluoromethyl) pyrimidine by Using 1,1,1,3,3-pentafluoro-3-methoxy-2-(trifluoromethyl)-propane Instead of 1,3,3,3-tetrafluoro-1-methoxy-2-(trifluoromethyl)-1-propene of Example 1

Under ice-water cooling, to 50 g of tetrahydrofuran were added 2 g (13.6 mmol) of 1-amidinopyrazole hydrochloride, 21.7 g (68.0 mmol) of potassium bis(trifluoromethanesulfonyl)imide and 3.6 g (15.6 mmol) of 1,1,1,3,3-pentafluoro-3-methoxy-2-(trifluoromethyl)-propane. Subsequently, a mixed solution of 11.4 g (88.4 mmol) of diisopropylethylamine and 10 g of tetrahydrofuran was added dropwise such that the internal temperature did not exceed 10° C., and the temperature was raised to room temperature. After about 16 hours, tetrahydrofuran was distilled off under reduced pressure, and then the residue was dissolved in ethyl acetate followed by column purification. The analysis results of the obtained compound were the same as those of the product of Example 1.

Example 4

Production of 6-fluoro-4-methoxy-2-(1-triazolyl)-5-(trifluoromethyl)pyrimidine by Using 1,1,1,3,3-pentafluoro-3-methoxy-2-(trifluoromethyl)-propane Instead of 1,3,3,3-tetrafluoro-1-methoxy-2-(trifluoromethyl)-1-propene of Example 2

Under ice-water cooling, to 50 g of tetrahydrofuran were added 2 g (13.6 mmol) of 1-amidinotriazole hydrochloride, 21.7 g (68.0 mmol) of potassium bis(trifluoromethanesulfonyl)imide and 3.6 g (15.6 mmol) of 1,1,1,3,3-pentafluoro-3-methoxy-2-(trifluoromethyl)-propane. Subsequently, a mixed solution of 11.4 g (88.4 mmol) of diisopropylethylamine and 10 g of tetrahydrofuran was added dropwise such that the internal temperature did not exceed 10° C., and the temperature was raised to room temperature. After about 16 hours, tetrahydrofuran was distilled off under reduced pressure, and then the residue was dissolved in ethyl acetate followed by column purification. The analysis results of the obtained compound were the same as those of the product of Example 2.

Example 5

Production of 6-fluoro-4-methoxy-2-(1-triazolyl)-5-(trifluoromethyl)pyrimidine by Using Sodium Tetraphenylborate Instead of Potassium bis(trifluoromethanesulfonyl)imide of Example 2

Under ice-water cooling, to 20 g of tetrahydrofuran were added 1 g (6.8 mmol) of 1-amidinotriazole hydrochloride, 9.2 g (27 mmol) of sodium tetraphenylborate and 1.7 g (7.8 mmol) of 1,3,3,3-tetrafluoro-1-methoxy-2-(trifluoromethyl)-1-propene. Subsequently, a mixed solution of 4.6 g (35 mmol) of diisopropylethylamine and 10 g of tetrahydrofuran was added dropwise such that the internal temperature did not exceed 10° C., and the temperature was raised to room temperature. After about 16 hours, tetrahydrofuran was distilled off under reduced pressure, and then the residue was dissolved in ethyl acetate followed by column purification. The analysis results of the obtained compound were the same as those of the product of Example 2.

In Examples 3 to 5, the isolated yields of the obtained compounds were not calculated, but in Examples 3 and 4, types and amounts of impurities are expected to be increased due to byproducts that can be generated in the course of producing 1,3,3,3-tetrafluoro-1-methoxy-2-(trifluoromethyl)-1-propene from 1,1,1,3,3-pentafluoro-3-methoxy-2-(trifluoromethyl)-propane in the reaction system. Therefore, the production methods of Examples 1 and 2 are conjectured to give high isolated yields of the obtained products as compared with the corresponding production methods of Examples 3 and 4. On the other hand, since in Example 5, the sodium salt that has a higher capacity of capturing fluoride ions than potassium, is used as the fluoride ion scavenger, the isolated yield of the obtained product is conjectured to be higher than that of the production method of Example 2.

Example 6

Production of 6-fluoro-2-(4-fluoro-1-pyrazolyl)-4-methoxy-5-(trifluoromethyl)pyrimidine 0.5 g (3.0 mmol) of 4-fluoro-1H-pyrazol-1-carboxyimideamide hydrochloride was dissolved in 8 ml of tetrahydrofuran, to this were added 4.5 g (14.0 mmol) of potassium bis(trifluoromethanesulfonyl)imide, 0.8 g (3.8 mmol) of 1,3,3,3-tetrafluoro-1-methoxy-2-(trifluoromethyl)-1-propene and 2.1 g (16.2 mmol) of diisopropylethylamine, and the mixture was stirred at room temperature for 16.7 hours. After stirring, the reaction solution was purified by a column to obtain 0.2 g (0.9 mmol) of the compound represented by the following formula (7) (chemical formula: $C_9H_5F_5N_4O$, molecular weight: 280.16 g/mol). The isolated yield of the obtained compound was 28.0%.

[Formula 11]

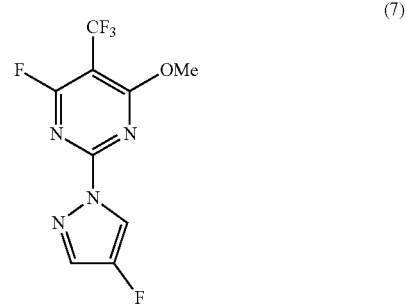

(7)

The analysis results were as follows.
Mass Spectrum (APCI, m/z): 280.9 ([M+H]$^+$)
$^1$H NMR (400 MHz, CDCl$_3$) δ ppm: 8.35 (dd, J=4.0, 0.9 Hz, 1H), 7.79 (dd, J=4.3, 0.6 Hz, 1H), 4.24 (s, 3H)

Example 7

Production of 6-fluoro-4-methoxy-2-(3-methyl-1-pyrazolyl)-5-(trifluoromethyl)pyrimidine 0.5 g (3.1 mmol) of 3-methyl-1H-pyrazol-1-carboxyimideamide hydrochloride was dissolved in 8.4 ml of tetrahydrofuran, to this were added 4.0 g (12.5 mmol) of potassium bis(trifluoromethanesulfonyl)imide, 0.8 g (3.8 mmol) of 1,3,3,3-tetrafluoro-1-methoxy-2-(trifluoromethyl)-1-propene and 2.1 g (16.2 mmol) of diisopropylethylamine, and the mixture was stirred at room temperature for 16.2 hours. After stirring, the reaction solution was purified by a column to obtain 0.6 g (2.1 mmol) of the compound represented by the following formula (8) (chemical formula: $C_{10}H_8F_4N_4O$, molecular weight: 276.19 g/mol). The isolated yield of the obtained compound was 67.0%.

[Formula 12]

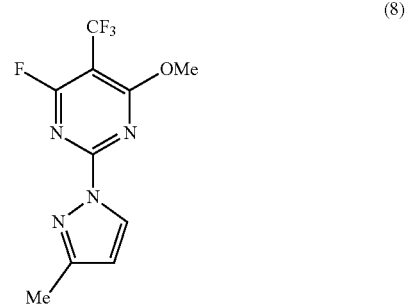

(8)

The analysis results were as follows.
Mass Spectrum (APCI, m/z): 277.1 ([M+H]$^+$)
$^1$H NMR (400 MHz, CDCl$_3$) δ ppm: 8.40 (d, J=2.6 Hz, 1H), 6.35 (d, J=2.8Hz, 1H), 4.23 (s, 3H), 2.42 (s, 3H)

TEST EXAMPLE OF BIOLOGICAL ACTIVITY

Evaluation Test for Rice Blast 6-fluoro-4-methoxy-2-(1-pyrazolyl)-5-(trifluoromethyl) pyrimidine prepared in Example 1 was dissolved in acetone to prepare a solution having a concentration of 100,000 ppm. Next, to 1 ml of this acetone solution was added sterilized water up to 50 ml to prepare a test solution having a concentration of 2,000 ppm. 1,000 μl of the test solution having a concentration of 2,000 ppm was added dropwise to a separately fabricated oatmeal culture medium, and air-dried. Subsequently, a 4-mm rice blast disc was placed such that flora contacted a treated surface of the oatmeal culture medium. Then, the oatmeal culture medium was allowed to stand still in a thermostatic room at 25° C. for 6 days, and an elongation length of hyphae was then investigated. The results are shown in Table 1. The preventive value was calculated according to the following expression. In the following expression, "without treatment" means that 1 ml of acetone was diluted with sterilized water to 50 ml as a test solution, and the solution was added dropwise to the culture medium. In addition, "with treatment" means that a test solution that had been diluted and adjusted to a set concentration was added dropwise to the culture medium.

TABLE 1

| Concentration of test solution (ppm) | Preventive value |
|---|---|
| 2000 | 100 |

Preventive value={(average of elongation lengths of hyphae without treatment−average of elongation lengths of hyphae with treatment)/average of elongation lengths of hyphae without treatment}×100 [Expression 1]

As shown in Table 1, the fluorine-containing pyrimidine compound of the present disclosure exhibits the control activity against the pathogens of rice blast, and is found to be effective as a compound exhibiting a biological activity.

The invention claimed is:

1. A fluorine-containing pyrimidine compound represented by the following formula (1):

[Formula 1]

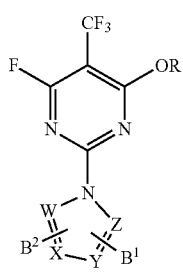

(1)

wherein

R represents a hydrocarbon group having 1 to 12 carbon atoms, $B^1$ and $B^2$ each independently represent a hydrogen atom, a halogen atom, a hydrocarbon group having 1 to 10 carbon atoms, $-C_nF_{2n+1}$ where n is an integer of 1 to 10, a nitro group, a boronic acid group, $-OA^1$, $-SO_mA^1$ where m is an integer of 0 to 3, $-NA^1A^2$, $-COOA^1$ or $-CONA^1A^2$, W, X, Y and Z each independently represent CV or N, V represents a hydrogen atom, a halogen atom, a hydrocarbon group having 1 to 10 carbon atoms, $-C_nF_{2n+1}$ where n is an integer of 1 to 10, a nitro group, a boronic acid group, $-OA^1$, $-SO_mA^1$ where m is an integer of 0 to 3, $-NA^1A^2$, $-COOA^1$ or $-CONA^1A^2$, and $A^1$ and $A^2$ each independently represent a hydrogen atom or a hydrocarbon group having 1 to 10 carbon atoms.

2. The fluorine-containing pyrimidine compound according to claim 1, wherein R is an alkyl group having 1 to 10 carbon atoms.

3. A method for producing a fluorine-containing pyrimidine compound of formula (1), comprising:

a step of reacting a fluoroisobutylene derivative represented by the following formula (2) with a compound represented by the following formula (3) or a salt thereof to obtain a fluorine-containing pyrimidine compound of the following formula (1):

[Formula 2]

(2)

(3)

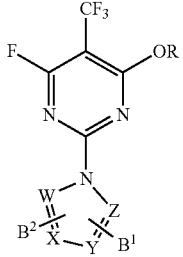

(1)

wherein

R represents a hydrocarbon group having 1 to 12 carbon atoms, $B^1$ and $B^2$ each independently represent a hydrogen atom, a halogen atom, a hydrocarbon group having 1 to 10 carbon atoms, $-C_nF_{2n+1}$ where n is an integer of 1 to 10, a nitro group, a boronic acid group, $-OA^1$, $-SO_mA^1$ where m is an integer of 0 to 3, $-NA^1A^2$, $-COOA^1$ or $-CONA^1A^2$, W, X, Y and Z each independently represent CV or N, V represents a hydrogen atom, a halogen atom, a hydrocarbon group having 1 to 10 carbon atoms, $-C_nF_{2n+1}$ where n is an integer of 1 to 10, a nitro group, a boronic acid group, $-OA^1$, $-SO_mA^1$ where m is an integer of 0 to 3, $-NA^1A^2$, $-COOA^1$ or $-CONA^1A^2$, and $A^1$ and $A^2$ each independently represent a hydrogen atom or a hydrocarbon group having 1 to 10 carbon atoms.

4. A method for producing a fluorine-containing pyrimidine compound of formula (1), comprising:

a step of reacting a fluoroisobutane derivative represented by the following formula (4) with a compound represented by the following formula (3) or a salt thereof to obtain a fluorine-containing pyrimidine compound of the following formula (1):

[Formula 3]

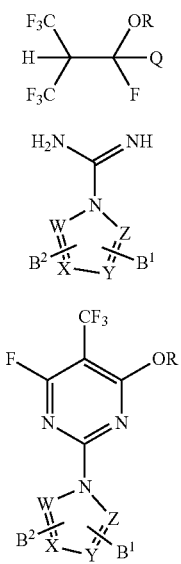

wherein

Q represents a halogen atom, —OA$^1$, —SO$_m$A$^1$ where m is an integer of 0 to 3, or —NA$^1$A$^2$, R represents a hydrocarbon group having 1 to 12 carbon atoms, B$^1$ and B$^2$ each independently represent a hydrogen atom, a halogen atom, a hydrocarbon group having 1 to 10 carbon atoms, —C$_n$F$_{2n+1}$ where n is an integer of 1 to 10, a nitro group, a boronic acid group, —OA$^1$, —SO$_m$A$^1$ where m is an integer of 0 to 3, —NA$^1$A$^2$, —COOA$^1$ or —CONA$^1$A$^2$, W, X, Y and Z each independently represent CV or N, V represents a hydrogen atom, a halogen atom, a hydrocarbon group having 1 to 10 carbon atoms, —C$_n$F$_{2n+1}$ where n is an integer of 1 to 10, a nitro group, a boronic acid group, —OA$^1$, —SO$_m$A$^1$ where m is an integer of 0 to 3, —NA$^1$A$^2$, —COOA$^1$ or —CONA$^1$A$^2$, and A$^1$ and A$^2$ each independently represent a hydrogen atom or a hydrocarbon group having 1 to 10 carbon atoms.

5. The method for producing a fluorine-containing pyrimidine compound according to claim 3, wherein R is an alkyl group having 1 to 10 carbon atoms.

6. The method for producing a fluorine-containing pyrimidine compound according to claim 4, wherein R is an alkyl group having 1 to 10 carbon atoms.

* * * * *